(12) United States Patent
Kim et al.

(10) Patent No.: US 11,400,127 B2
(45) Date of Patent: Aug. 2, 2022

(54) METHOD FOR PROCESSING GINSENG WITH ULTRA-HIGH PRESSURE

(71) Applicant: NUTREX TECHNOLOGY CO., LTD., Seongnam-si (KR)

(72) Inventors: Sung Han Kim, Seoul (KR); Jun Yong Jang, Seongnam si (KR); Sang Ho Lee, Daejeon (KR); Sung Yul Yoo, Seoul (KR)

(73) Assignee: NUTREX TECHNOLOGY CO., LTD., Seongnam-si (KR)

( * ) Notice: Subject to any disclaimer, the term of this patent is extended or adjusted under 35 U.S.C. 154(b) by 78 days.

(21) Appl. No.: 16/638,984

(22) PCT Filed: Mar. 16, 2018

(86) PCT No.: PCT/KR2018/003083
§ 371 (c)(1),
(2) Date: Feb. 13, 2020

(87) PCT Pub. No.: WO2019/035525
PCT Pub. Date: Feb. 21, 2019

(65) Prior Publication Data
US 2020/0360456 A1    Nov. 19, 2020

(30) Foreign Application Priority Data
Aug. 14, 2017  (KR) .......................... 10-2017-0103194

(51) Int. Cl.
*A61K 36/258*   (2006.01)
(52) U.S. Cl.
CPC .................................. *A61K 36/258* (2013.01)
(58) Field of Classification Search
CPC .......... A23V 2250/212; A23V 2300/10; A23V 2300/46; A23V 2002/00; A23V 2250/2124; A23L 5/30; A23L 19/10; A23L 5/13; A23L 5/17; A61K 36/258
See application file for complete search history.

(56) References Cited

FOREIGN PATENT DOCUMENTS

| KR | 10-2003-0087250 A | 11/2003 |
| KR | 10-2010-0069194 A | 6/2010 |
| KR | 10-2011-0013204 A | 2/2011 |
| KR | 10-2011-0131698 A | 12/2011 |
| KR | 10-1397145 B1 | 5/2014 |
| KR | 10-1827272 B1 | 2/2018 |

OTHER PUBLICATIONS

Tao D; Li F; Hu X; Liao X; Zhang Y "Quality comparison of 'Laba' garlic processed by High Hydrostatic Pressure and High Pressure Carbon Dioxide" (pub online Feb. 28, 2020) 10:3719, 9 pages; doi.org/10.1038/s41598-020-60667-2/. (Year: 2020).*
International Search Report for PCT/KR2018/003083 dated Jun. 27, 2018 [PCT/ISA/210].

* cited by examiner

*Primary Examiner* — Aaron J Kosar
(74) *Attorney, Agent, or Firm* — Sughrue Mion, PLLC

(57) ABSTRACT

The present invention relates to a method for processing *ginseng* at an ultra high pressure, and more particularly, to a method for processing *ginseng* that is capable of processing the *ginseng*, which is immersed and packed, at an ultra high pressure. The method for processing *ginseng* includes the steps of: preparing washed *ginseng*; liquid-packaging the *ginseng* into a pouch; and treating the liquid-packaged *ginseng* with ultra-high pressure at a pressure of 550 to 600 MPa for 30 seconds to 2 minutes.

10 Claims, 4 Drawing Sheets

METHOD FOR PROCESSING GINSENG WITH ULTRA-HIGH PRESSURE

CROSS REFERENCE TO RELATED APPLICATIONS

This application is a National Stage of International Application No. PCT/KR2018/003083 filed Mar. 16, 2018, claiming priority based on Korean Patent Application No. 10-2017-0103194 filed Aug. 14, 2017.

TECHNICAL FIELD

The present invention relates to a method for processing *ginseng* at an ultra high pressure, and more particularly, to a method for processing *ginseng* that is capable of processing the *ginseng*, which is immersed and packed, at an ultra high pressure.

BACKGROUND ART

*Ginseng* is a root of *Panax ginseng* C.A. Meyer of Araliaceae, from which fine roots and a cork layer are removed. The *ginseng* is taken as decoction in Oriental medicine, and recently, *ginseng* products capable of conveniently taken, have been developed to increase amounts of *ginseng* consumed.

One of products, which occupies the biggest market of processed foods using *ginseng*, is a red *ginseng* product, and in the same manner as red *ginseng*, particularly, pouch, pill, jelly, candy, and milk products, which are made of a red *ginseng* extract, have been actively introduced.

A main additive material in making such various products is the red *ginseng* extract which is produced from red *ginseng* having a water content of less than 15% after *ginseng* has been steamed and dried by means of hot water extraction or water/ethanol extraction. Because of high-priced material characteristics of the red *ginseng*, very high profits can be obtained even in a change of 5% of yield. Improving the yield of the red *ginseng* extract produced from the red *ginseng* is the most important thing in making the red *ginseng* products. So as to improve the extraction yield of the red *ginseng* extract, however, many extraction times have to be required, which causes losses in time and cost, and accordingly, there is a need for improvement of the extraction yield in the industrial fields through efficient methods.

To do this, a conventional method for increasing yield of a red *ginseng* extract by means of enzyme dissolution of *ginseng* generated upon heat treatment of the *ginseng* is disclosed in Korean Patent Application Laid-open No. 10-2001-0038803. Only when the red *ginseng* made through the heat treatment is pulverized to a size of less than 120 mesh, however, the extraction efficiency of the red *ginseng* extract is improved. So as to allow the conventional method to be applied industrially, accordingly, additional equipment and time for the pulverization process before the extraction is carried out are required. Further, the extraction from the pulverized red *ginseng* powder may cause caking of the powder, and accordingly, no gentle filtering is obtained. As a result, the conventional method is not proper in the industrial use.

Another conventional method for making *ginseng* and red *ginseng* is disclosed in Korean Patent No. 10-0445184, and according to the conventional method, the *ginseng* is subjected to an ultra high pressure treatment to increase an extraction yield of ginsenosides and to contain specific saponins.

During the ultra high pressure treatment, however, the *ginseng* may be deformed in shape, and also, a vacuum packing material may be broken by the fine roots of *ginseng*. Accordingly, there is a need for a novel method for processing *ginseng* at an ultra high pressure so as to stably improve the extraction yield of ginsenosides, while giving no influence on shape of *ginseng*.

Accordingly, the present inventors have found that if *ginseng* is immersed, packed and processed with ultra-high pressure, it can be maintained in shape and the extraction yield of ginsenosides is higher than that in the ultra high pressure treatment in the conventional practices, without having any problems in the *ginseng* processing, and after that, they have finished the method for processing *ginseng* according to the present invention.

DISCLOSURE

Technical Problem

It is an object of the present invention to provide a method for processing *ginseng*.

It is another object of the present invention to provide a *ginseng* extract that is produced through a method for processing *ginseng* according to the present invention.

The technical problems to be achieved through the present invention are not limited as mentioned above, and other technical problems not mentioned herein will be obviously understood by one of ordinary skill in the art through the following description.

Technical Solution

To accomplish the above-mentioned objects, according to one aspect of the present invention, there is provided a method for processing *ginseng*, including the steps of: preparing washed *ginseng*; liquid-packaging the *ginseng* into a pouch; and treating the liquid-packaged *ginseng* with ultra-high pressure at a pressure of 550 to 600 MPa for 30 seconds to 2 minutes.

According to the present invention, desirably, the immersed packing is carried out by putting a solvent and the *ginseng* in the pouch, removing air from the pouch, and sealing the pouch. At this time, further, the solvent is water or ethanol, the pouch is made of one selected from the group consisting of LDPE, LLDPE, HDPE, PP, PS, PVC, SBS, and PE, and the pouch has a thickness of 1 to 2 mm.

According to the present invention, desirably, the ultra high pressure treatment is carried out by secondarily packing the pouch with the immersed and packed *ginseng* with a shock absorbing container.

According to the present invention, desirably, the method further includes, after the ultra high pressure treatment, the steps of: steaming the *ginseng* at a temperature of 96 to 98° C. for 1 to 1.2 hours; and drying the steamed *ginseng* at a temperature of 50 to 60° C. for 72 to 96 hours.

According to the present invention, desirably, the method further includes, after the drying step, the step of: putting the dried *ginseng* in an extraction solvent, heating the *ginseng* in the extraction solvent at a temperature of 46 to 53° C. for 8 to 9 hours, and producing a *ginseng* extract. At this time, the extraction solvent is mixed with the solvent in the pouch collected after the ultra high pressure treatment.

To accomplish the above-mentioned objects, according to another aspect of the present invention, there is provided a ginseng extract produced by a method for processing ginseng, the method including the steps of: preparing washed ginseng; liquid-packaging the ginseng into a pouch; treating the liquid-packaged ginseng with ultra-high pressure at a pressure of 550 to 600 MPa for 30 seconds to 2 minutes; steaming the ginseng after the ultra high pressure treatment at a temperature of 96 to 98° C. for 1 to 1.2 hours; drying the steamed ginseng at a temperature of 50 to 60° C. for 72 to 96 hours; and putting the dried ginseng in an extraction solvent, heating the ginseng in the extraction solvent at a temperature of 46 to 53° C. for 8 to 9 hours, and producing the ginseng extract.

According to the present invention, desirably, the ginseng extract contains ginsenoside contents more than 2 wt % through two extraction times.

Advantageous Effects

According to the present invention, the method for processing the ginseng is carried out by putting the washed ginseng into the pouch where the solvent is put and treating the liquid-packaged ginseng with ultra-high pressure, so that the solvent in the pouch is re-used with the extraction solvent in the extraction process of the ginseng extract in the future, thereby preventing the effective ingredients of the ginseng existing in the solvent of the pouch from being consumed and thus increasing contents of ginsenosides of the ginseng extract finally produced.

In addition, the method according to the present invention can solve the problems occurring in the ultra high pressure treatment through vacuum packing as the conventional ginseng processing method, such as deformation of ginseng in shape, breakage of a vacuum packing material, and so on.

Further, the method according to the present invention can solve the problem occurring in the ultra high pressure treatment through vacuum packing in the conventional practice, thereby preventing the pouch from being broken due to the application of the external pressure to the outward protruding fine roots of the ginseng and thus keeping the ginseng processing in a more stable state.

Furthermore, the method according to the present invention is carried out by liquid-packaging the ginseng so that a surface area applying a pressure to the ginseng becomes larger than that in the ultra high pressure treatment through the vacuum packing in the conventional practice, thereby performing the ultra high pressure treatment more effectively.

The effects of the invention are not limited as mentioned above, and it should be understood that the effects of the invention include all effects inferable from the detailed description and claims of the present invention.

BEST MODE FOR INVENTION

Figure 1:
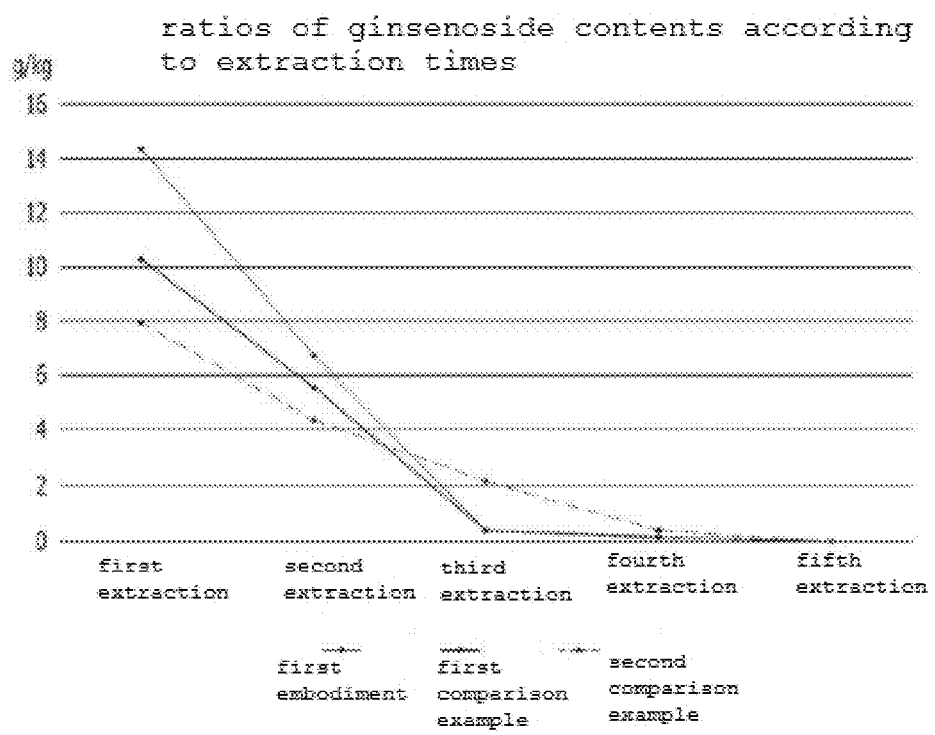
FIG. 1 is a graph showing when a ginseng extract is produced five times through a method for processing ginseng according to the present invention, ratios of contents of ginsenosides extracted according to the respective extraction times.

Hereinafter, the present invention will be in detail explained with reference to the attached drawings.

According to the present invention, a method for processing ginseng includes the steps of preparing washed ginseng, liquid-packaging the ginseng into a pouch, and treating the liquid-packaged ginseng with ultra-high pressure at a pressure of 550 to 600 MPa for 30 seconds to 2 minutes.

Now, the method for processing ginseng according to the present invention will be in detail explained according to the respective steps.

First, the method for processing ginseng according to the present invention includes the step of preparing washed ginseng.

At this time, the ginseng is fresh ginseng which is not processed at all, but it is in a natural state, while being not dried or steamed. The fresh ginseng may be harvested after cultivated for 4 to 6 years, and according to the present invention, desirably, the fresh ginseng is four-years-old fresh ginseng. Also, the fresh ginseng may become cultivated ginseng artificially growing in a ginseng field, wild cultivated ginseng naturally growing with wild ginseng from seeds scattering in deep mountains, or wild ginseng growing naturally in deep mountains. Further, the ginseng may become Korean ginseng produced in Korea, Panax quinquefolium produced in North America like U.S.A. and Canada, Panax notoginseng produced in China, and Panax japonicus produced in Japan, and in addition thereto, of course, the ginseng may become different kinds of ginseng, without any specific limitation in the cultivation areas. In the description of the present invention, therefore, it has to be appreciated that the ginseng includes various kinds of ginseng as mentioned above and red ginseng made through steaming and drying.

Before washing the ginseng, a separation step in which stems and leaves are removed may be carried out. In detail, the separation step is to separate the stems and leaves from the roots of the ginseng after the ginseng has been collected. The stems and leaves of the ginseng may be used as products through a separate step, and the roots of the ginseng separated from the stems and leaves are separated for the method for processing the ginseng according to the present invention. However, the separation step may be removed according to objects to be achieved, and without any separation step, accordingly, the ginseng inclusive of the stems and leaves may be used in the method for processing the ginseng according to the present invention.

On the other hand, the washing step serves to remove foreign matters attached to the cultivated ginseng from the ginseng. At this time, the washing step includes both of a washing step through water, a water-soluble solvent, or a fat-soluble solvent and a typical washing step carried out in a general ginseng washing process. For example, the washing step includes vibration washing using bubbles of water, washing carried out by primarily washing the ginseng with wash water flowing and secondarily washing the ginseng with ultrasonic waves, soaking washing carried out by soaking the fronts and backs of the *ginseng* alternately in wash water, or washing carried out by primarily soaking the fronts and backs of the *ginseng* alternately in wash water and then secondarily washing the *ginseng* with water flowing. In addition thereto, of course, if a washing step is carried out to remove the foreign matters from the *ginseng*, without any damage in the *ginseng*, the washing step can be freely used, without any particular limitation.

Referring in more detail to the washing step as mentioned above, the vibration washing using bubbles of water is carried out by putting the *ginseng* into a water tank to allow the *ginseng* to be washed through the vibration of the air bubbles in water through an operation of an air blower and an ozone ($O_3$) generator. Further, the washing carried out by primarily washing the *ginseng* with wash water flowing and secondarily washing the *ginseng* with ultrasonic waves is carried out by putting the *ginseng* into a washing tank, primarily washing the *ginseng* with the wash water flowing, and secondarily washing the *ginseng* with the ultrasonic waves generated from an ultrasonic converter located under the washing tank, so that during the washing process, impurities attached to the *ginseng* are removed by means of the flowing wash water, and also, heavy metals and residual pesticides, which may exist in the *ginseng*, are removed from the surfaces of the *ginseng* by means of the ultrasonic waves generated from the ultrasonic converter. The soaking washing or the washing with the flowing water is repeatedly carried out for about 30 seconds to 2 minutes on a condition where the *ginseng* is not damaged.

The examples of the washing step as mentioned above are applied to cleanly wash the *ginseng* before the method for processing the *ginseng* according to the present invention is carried out, and therefore, they do not limit the scope of the present invention. If the washing step is the *ginseng* washing method generally used, the examples of the washing step can be all used, without any limitation.

Next, the method for processing *ginseng* according to the present invention includes the step of liquid-packaging the *ginseng* into a pouch.

At this time, the immersed packing means that after a solvent and the *ginseng* are put in the pouch, the pouch is sealed. In this case, sealing is carried out by removing air from the pouch so as to perform the ultra high pressure treatment.

According to the present invention, the immersed packing can solve the problems occurring in the ultra high pressure treatment through vacuum packing as the conventional *ginseng* processing method, such as deformation in shape of *ginseng*, breakage of a vacuum packing material, and so on. In detail, the *ginseng* is immersed and packed together with the solvent in the pouch, and accordingly, empty spaces, which may be formed among the *ginseng* in the pouch, are filled with the solvent, thereby forming a complete vacuum state. As a result, the immersed packing can prevent the *ginseng* from being deformed in shape in the empty spaces of the pouch by means of external pressure when the *ginseng* is subjected to the ultra high pressure treatment in the conventional vacuum packing method. Further, the immersed packing can prevent the fine roots of the *ginseng* from protruding outward to thus cause the pouch to be broken by means of the external pressure upon the ultra high pressure treatment through vacuum packing in the conventional *ginseng* processing method, thereby keeping the *ginseng* processing in a more stable state. Furthermore, the immersed packing has a surface area applying a pressure to the *ginseng* larger than that in the ultra high pressure treatment in the conventional vacuum packing method, thereby performing the ultra high pressure treatment more effectively.

Moreover, the immersed packing is carried out by putting the washed *ginseng* into the pouch where the solvent is put before the ultra high pressure treatment is applied, so that effective ingredients, which can be extracted from the *ginseng* to the solvent during the ultra high pressure treatment, cannot be consumed. In detail, the solvent in the pouch is re-used with an extraction solvent in an extraction process of a *ginseng* extract in the future, so that the effective ingredients of the *ginseng* existing in the solvent of the pouch is not consumed at all, thereby improving contents of ginsenosides of the *ginseng* extract finally produced.

If the *ginseng* not vacuum packed, but immersed and packed is subjected to the ultra high pressure treatment, further, residual air existing in the packing material is dissolved by the solvent at a high pressure, so that the packing material is not broken due to the residual air existing therein, and also, an increasing speed up to the ultra high pressure is not decreased, thereby performing the ultra high pressure treatment rapidly and efficiently and making it possible to perform the ultra high pressure treatment for large amounts of *ginseng*.

Water or ethanol may be used as the solvent, and the pouch is made of one selected from the group consisting of LDPE, LLDPE, HDPE, PP, PS, PVC, SBS, and PE. If the pouch is not broken in the range of the pressure as suggested in the present invention and is capable of cutting off the movements between the solvent therein and materials on the outside thereof, however, it may be freely used in kind, without any particular limitation.

On the other hand, the pouch has a thickness of 0.5 to 3 mm or 0.5 to 2.5 mm, and desirably, the pouch has a thickness of 1 to 2 mm. So as to perform the ultra high pressure treatment for large amounts of *ginseng*, above all, the thickness of the pouch is substantially high, which is over a thickness of a general vinyl pouch.

Further, a volume of the pouch desirably is greater by about 130 to 140% than a volume of the *ginseng* to be processed, but of course, the volume of the pouch may be freely changed according to amounts of *ginseng* to be processed.

Also, the sealing is carried out by thermally treating an inlet portion of the pouch, through which the solvent and the *ginseng* are put, or tying the inlet portion of the pouch with a cable tie. The sealing may be freely carried out, without any particular limitation.

Next, the method for processing *ginseng* according to the present invention includes the step of treating the liquid-packaged *ginseng* with ultra-high pressure at a pressure of 550 to 600 MPa for 30 seconds to 2 minutes.

At this time, the pressure is desirably in the range of 550 to 600 MPa, but also, the pressure may be in the range of 500 to 650 MPa or in the range of 450 to 700 MPa.

Further, the ultra high pressure treatment time is desirably in the range of 30 seconds to 2 minutes, but of course, the time is in the range of 20 seconds to 5 minutes or in the range of 10 seconds to 10 minutes.

However, the pressure and the ultra high pressure treatment time may be freely changed according to the objects to be achieved, without any particular limitations.

Also, the ultra high pressure treatment is characterized in that the pouch with the immersed and packed *ginseng* is secondarily packed with a shock absorbing container.

In the secondary packing, at this time, the immersed packing is carried out by primarily putting the pouch in the shock absorbing container, by putting the *ginseng* in the pouch, by putting the solvent in the pouch, and by sealing the pouch. In the opposite order to the above-mentioned order, of course, the immersed packing is carried out by primarily putting the *ginseng* in the pouch, by putting the pouch where the *ginseng* is put in the shock absorbing container, by putting the solvent in the pouch, and by sealing the pouch. The order of the immersed packing and the secondary packing is not limited particularly thereto.

The shock absorbing container is used to prevent the deformation in shape of the *ginseng* and the breakage of the pouch due to the collision between the *ginseng* and an ultra high pressure treatment device upon the ultra high pressure treatment. If the shock absorbing container does not exist, there is a possibility that the pouch with the immersed and packed *ginseng* may be broken due to the impact generated during the ultra high pressure treatment, thereby making it difficult to perform the ultra high pressure treatment for large amounts of *ginseng*.

At this time, the shock absorbing container is made of a Toilon material. However, the shock absorbing container is not limited thereto, but if it absorbs the impact caused by the collision against the pouch and the *ginseng* and transfers a pressure produced from the ultra high pressure treatment device to the pouch, it can be freely used, without any particular limitation. The shock absorbing container has a shape of a cylinder, but it is not particularly limited in shape. Further, the shock absorbing container desirably has a size spaced apart from the pouch with the immersed and packed *ginseng* by a distance of about 1 to 2 cm.

The pouch with the immersed and packed *ginseng* is secondarily packed with the shock absorbing container and is then put in a casing for the ultra high pressure treatment. Through the use of the shock absorbing container, the direct collision between the casing and the pouch is prevented to allow the *ginseng* processing to be achieved more stably.

The ultra high pressure treatment serves to destruct the cells in the *ginseng* through the application of the ultra high pressure, thereby enhancing an extraction efficiency in the *ginseng* extraction process in the future. In detail, the cells in the *ginseng* are destructed through the ultra high pressure treatment, thereby making it easy to extract the effective ingredients of the *ginseng* like ginsenosides existing in the cells and increasing the amounts of the effective ingredients of the *ginseng* in the *ginseng* extract produced through the *ginseng* extract producing process in the future. At this time, the effective ingredients of the *ginseng* mean various bioactive compositions that can be extracted from the *ginseng*. In detail, the effective ingredients of the *ginseng* include ginsenosides, polysaccharide, polyacetylene, phenolic compounds, alkaloid, carbohydrate, and amino acid.

According to the present invention, further, the method for processing the *ginseng* includes the steps of steaming, after the ultra high pressure treatment, the *ginseng* at a temperature of 96 to 98° C. for 1 to 1.2 hours and drying the steamed *ginseng* at a temperature of 50 to 60° C. for 72 to 96 hours.

The steaming step is carried out by steaming the *ginseng* after the ultra high pressure treatment so as to process the *ginseng* to red *ginseng*, and accordingly, the steaming step may be carried out in a typically known method in the art, for example, by arranging the *ginseng* in a steamer in such a manner as to be not pushed or laid on each other and by then heating the *ginseng*.

The steaming step is carried out at a temperature of 92 to 102° C. for 60 to 108 hours or at a temperature of 94 to 100° C. for 66 to 102 hours, and desirably, the steaming step is carried out at a temperature of 96 to 98° C. for 72 to 96 hours.

At this time, if the steaming temperature is lower than 92° C. or the steaming time is less than 60 hours, the steaming is not sufficiently performed, thereby decreasing an amount of crude saponin in the *ginseng*, and contrarily, if the steaming temperature is lower than 102° C. or the steaming time is more than 108 hours, the steaming is excessively performed, thereby decreasing an amount of crude saponin in the *ginseng*.

In addition to the ranges as mentioned above, however, the steaming temperature and time are freely changed according to the objects to be achieved, without any particular limitations.

Before the *ginseng* whose steaming is finished is dried, on the other hand, a pressure of the steamer can be lowered. At this time, if the pressure of the steamer is suddenly lowered, the body of the steamed *ginseng* may be broken, and accordingly, the steam is slowly discharged from the steamer. Otherwise, the steamer is naturally abandoned until the pressure becomes a normal pressure.

The drying step is carried out by drying the steamed *ginseng* by means of heating or air blowing, and through the drying, the surface of the *ginseng* is dried and serves as a blocking film, thereby suppressing volatile effective ingredients of the *ginseng* from being volatilized. The drying step may be carried out in a typically known method in the art, for example, by arranging the *ginseng* in a dryer in such a manner as to be not pushed or laid on each other and by then heating or air-blowing the *ginseng*.

The drying step is carried out at a temperature of 40 to 70° C. for 60 to 108 hours or at a temperature of 45 to 75° C. for 66 to 102 hours, and desirably, the drying step is carried out at a temperature of 50 to 60° C. for 72 to 96 hours.

At this time, if the drying temperature is lower than 40° C. or the drying time is less than 60 hours, the drying is not sufficiently performed, thereby causing the surface of the *ginseng* to be not dried sufficiently and thus making the volatile effective ingredients of the *ginseng* volatilized. As the drying is not sufficiently performed, further, a content of water in the *ginseng* increases to cause microorganisms like mold (fungi) to be cultivated upon storage. On the other hand, if the drying temperature is higher than 70° C. or the drying time is less than 108 hours, the drying is excessively performed, thereby making extraction in the future extraction process not performed well.

In addition to the ranges as mentioned above, however, the drying temperature and time are freely changed according to the objects to be achieved, without any particular limitations.

According to the present invention, also, the steaming step and the drying step are repeatedly carried out two to five times, and of course, they may be repeatedly carried out five times or more according to the objects to be achieved.

According to the present invention, further, the method for processing the *ginseng* includes the step of putting the dried *ginseng* in an extraction solvent, heating the *ginseng* in the extraction solvent at a temperature of 46 to 53° C. for 8 to 9 hours, and producing a *ginseng* extract.

The extraction step is the step of extracting the effective ingredients of the *ginseng* inclusive of the ginsenosides from the *ginseng* after the steaming and drying steps. The extraction step may be carried out in a typically known method in the art, for example, by putting the *ginseng* in an extraction container together with the solvent and heating the *ginseng*.

At this time, the extraction solvent includes one selected from water, ethanol, chloroform, ethyl ether, acetone, and petroleum ether, and desirably, the extraction solvent is water or ethanol.

Also, the extraction solvent is characterized in that it is mixed with the solvent in the pouch collected after the ultra high pressure treatment.

According to the present invention, small amounts of effective ingredients of the *ginseng* may extractedly enter the solvent of the pouch upon the ultra high pressure treatment, and accordingly, the solvent of the pouch is re-used together with the extraction solvent at the extraction step, thereby preventing the small amounts of effective ingredients of the *ginseng* from being consumed and thus increasing the contents of the ginsenosides in the *ginseng* extract finally produced.

The heating step of heating the *ginseng* in the extraction solvent is carried out at a temperature of 40 to 59° C. for 6 to 11 hours or at a temperature of 43 to 56° C. for 7 to 10 hours, and desirably, the heating step is carried out at a temperature of 46 to 53° C. for 8 to 9 hours.

The extraction step is several times carried out to increase the contents of the effective ingredients extracted from the *ginseng*. According to the present invention, at this time, contents of the ginsenosides with respect to the total weight of the *ginseng* extract can be more than 2 wt % only through two times extraction. According to the present invention, the cells in the *ginseng* are broken through the ultra high pressure treatment before the steaming and extracting steps of the *ginseng*, so that it is easy to extract the effective ingredients of the *ginseng* inclusive of the ginsenosides in the cells, thereby allowing the effective ingredients of the *ginseng* to be extracted in relative large amounts at the extraction step.

According to another aspect of the present invention, further, there is provided a *ginseng* extract produced through a method for processing *ginseng* including the steps of preparing washed *ginseng*, liquid-packaging the *ginseng* into a pouch, treating the liquid-packaged *ginseng* with ultra-high pressure at a pressure of 550 to 600 MPa for 30 seconds to 2 minutes, steaming the *ginseng* to which the ultra high pressure treatment is applied at a temperature of 96 to 98° C. for 1 to 1.2 hours, drying the steamed *ginseng* at a temperature of 50 to 60° C. for 72 to 96 hours, and putting the dried *ginseng* in an extraction solvent, heating the *ginseng* in the extraction solvent at a temperature of 46 to 53° C. for 8 to 9 hours, and producing the *ginseng* extract.

At this time, the method for processing *ginseng* so as to produce the *ginseng* extract can be carried out in the same conditions as that as mentioned above.

On the other hand, the contents of the ginsenosides in the *ginseng* extract are more than 2 wt % only through two times extraction. For example, if it is desired to produce a *ginseng* extract from 1 kg of *ginseng* through the method for processing the *ginseng* according to the present invention, the contents of the ginsenosides in the *ginseng* extract can be more than 20 g only through two times extraction.

Figure 2:
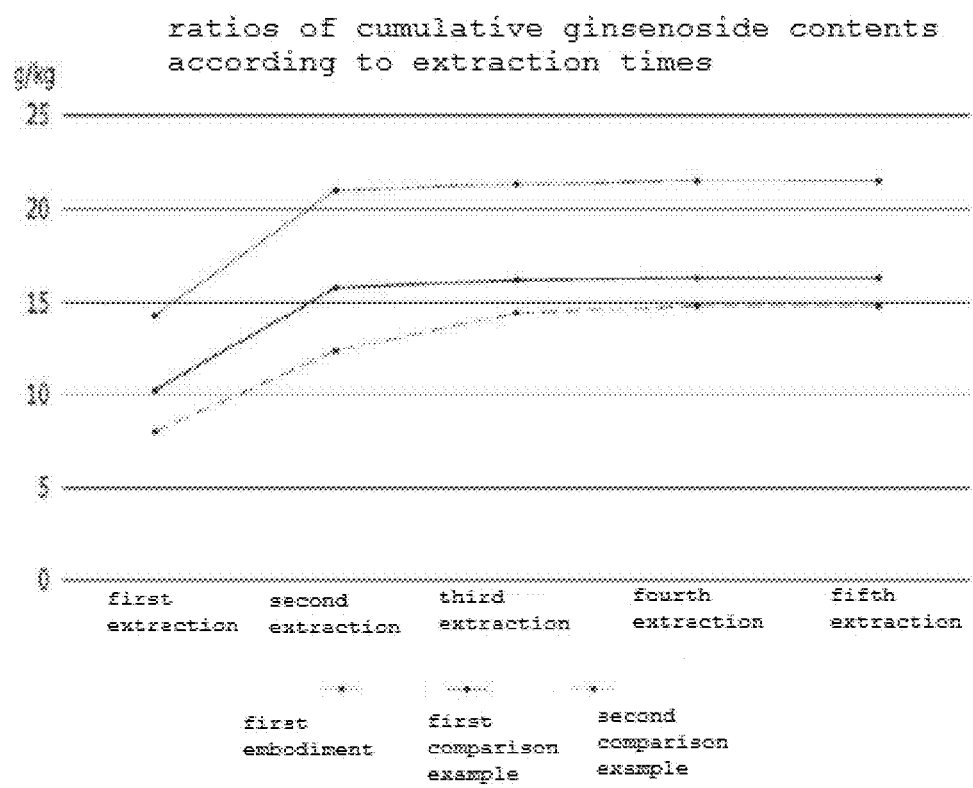
FIG. 2 is a graph showing when a ginseng extract is produced five times through a method for processing ginseng according to the present invention, ratios of contents of ginsenosides accumulatedly extracted according to the respective extraction times.

According to the present invention, before the steaming and extracting steps of the *ginseng*, the cells in the *ginseng* are broken through the ultra high pressure treatment so that it is easy to extract the effective ingredients of the *ginseng* inclusive of the ginsenosides in the cells, thereby providing a higher extraction ratio than the existing extraction ratio at the extraction step. Also, the *ginseng* extract having large contents of the effective ingredients can be produced just with the extraction times smaller than the existing extraction times. As shown in FIG. 2, in detail, it can be appreciated that the contents of the ginsenosides in the *ginseng* extract produced through two times extraction after the *ginseng* has been subjected to the ultra high pressure treatment are larger than the contents of the ginsenosides in the *ginseng* extract produced through five times extraction after the *ginseng* has been not subjected to the ultra high pressure treatment (See First experimental example).

First Producing Example: Washing *Ginseng*

Four-years-old fresh *ginseng* cultivated on Keumsan, Chungnam in Korea was put and washed into a rotary type high pressure tumbler washer, and next, stems and leaves were removed from the fresh *ginseng*, thereby preparing the washed fresh *ginseng*.

First Embodiment: First Production of Red *Ginseng*Extract

A red *ginseng* extract was produced from the fresh *ginseng* through the method for processing the *ginseng* according to the present invention.

First Step: Ultra High Pressure Treatment

Figure 3:
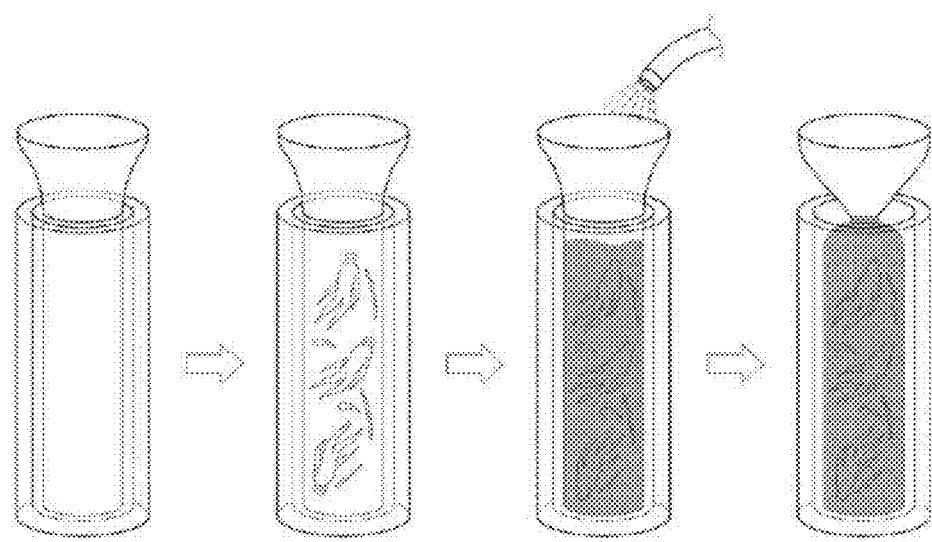
FIG. 3 is a flow diagram showing the step of liquid-packaging the ginseng in the method for processing ginseng according to the present invention.

FIG. 3 is a flow diagram showing the step of liquid-packaging *ginseng* according to the present invention. Through the step as shown in FIG. 3, the fresh *ginseng* was immersed and packed.

First, a pouch made of a PE material and having a height of about 1.5 m and a width of about 2.5 m was put into a shock absorbing container made of a Toilon material and having a height of about 0.85 m and a width of about 0.23 m, and next, a space was formed in the interior of the pouch so as to put the fresh *ginseng* therein.

Next, 450 kg of fresh *ginseng*, which was washed according to the first producing example, was put into the pouch, and water was poured into the pouch until the fresh *ginseng* was filled with the water.

After that, air bubbles existing in the pouch were removed, and the inlet portion of the pouch was sealedly tied with a cable tie.

Figure 4A:
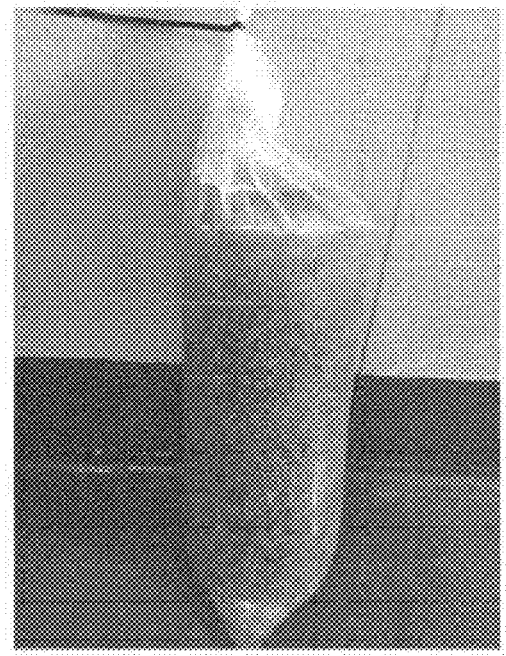
FIG. 4A is a photograph showing a pouch, in which water and fresh ginseng are put, is sealed in the method for processing ginseng according to the present invention.

FIG. 4A is a photograph showing a pouch, in which water and fresh *ginseng* are put, is sealed in the method for processing *ginseng* according to the present invention. As shown in FIG. 4A, it can be appreciated that the method for processing the *ginseng* according to the present invention is capable of applying the ultra high pressure treatment to large amounts of *ginseng* through one time packing.

The shock absorbing container in which the pouch was put was inserted into a casing of an ultra high pressure treatment device, and the fresh *ginseng* put in the pouch was subjected to the ultra high pressure treatment at a room temperature and a pressure of about 550 MPa for 2 minutes.

Second Step: Steaming and Drying

The fresh *ginseng*, to which the ultra high pressure treatment was applied through the first step, was arranged in a steamer in such a manner as to be not pushed or laminated onto each other, and next, the fresh *ginseng* was steamed through heating at a temperature of 96° C. for 1 hour. After the steaming was finished, a pressure of the steamer was released to remove steam and thus to obtain red *ginseng*.

Next, the red *ginseng* was arranged in a drier in such a manner as to be not pushed or laminated onto each other, and after that, the red *ginseng* was dried through heating at a temperature of 60° C. for 72 to 96 hours.

Third Step: Red*Ginseng*Extract Producing

An ethanol solvent was mixed with the solvent of the pouch used for the ultra high pressure treatment at the first step so as to make an extraction solvent. The red *ginseng* made through the second step was put into an extraction container of an extractor, and also, the extraction solvent was put thereinto. Next, the red *ginseng* was heated at a temperature of 46 to 53° C. for 8 to 9 hours to produce a red *ginseng* extract.

The extraction step was repeated five times, and the red *ginseng* extracts were produced individually according to the respective extraction times.

Amounts of red *ginseng* extracts produced according to the respective extraction times were listed in Table 1.

TABLE 1

| Extraction times | Red ginseng extract weight (kg) | Red ginseng extract cumulative weight (kg) |
| --- | --- | --- |
| First time | 260 | 260 |
| Second time | 51 | 311 |
| Third time | 32 | 343 |
| Fourth time | 32 | 375 |
| Fifth time | 22 | 397 |

First Comparison Example: Second Production of Red Ginseng Extract

A red *ginseng* extract was produced from the fresh *ginseng* according to a method for processing the *ginseng* at an ultra high pressure through vacuum packing.

First Step: Ultra High Pressure Treatment

First, 2 kg of fresh *ginseng*, which was washed according to the first producing example, was put into a pouch made of a PE material and having a height of about 0.5 m and a width of about 0.3 m and then sealed in a state of being vacuumed by means of a vacuum packing machine.

Figure 4B:
FIG. 4B is a photograph showing a bag, in which fresh ginseng is put, is vacuum packed.

FIG. 4B is a photograph showing a bag, in which fresh *ginseng* is put, is vacuum packed. As appreciated from FIG. 4B, disadvantageously, the ultra high pressure treatment through the vacuum packing can be applied only to small amounts of *ginseng* to be packed one time.

Next, the pouch was put into a casing of an ultra high pressure treatment device, and the fresh *ginseng* put in the pouch was subjected to the ultra high pressure treatment at a room temperature and a pressure of about 550 MPa for 2 minutes.

Second Step: Steaming and Drying

The fresh *ginseng*, to which the ultra high pressure treatment was applied through the first step, was arranged in a steamer in such a manner as to be not pushed or laminated onto each other, and next, the fresh *ginseng* was steamed through heating at a temperature of 96° C. for 1 hour. After the steaming was finished, a pressure of the steamer was released to remove steam and thus to obtain red *ginseng*.

Next, the red *ginseng* was arranged in a drier in such a manner as to be not pushed or laminated onto each other, and after that, the red *ginseng* was dried through heating at a temperature of 60° C. for 72 to 96 hours.

Third Step: Red*Ginseng*Extract Producing

The red *ginseng* made through the second step was put into an extraction container of an extractor, and also, ethanol as an extraction solvent was put thereinto. Next, the red *ginseng* was heated at a temperature of 46 to 53° C. for 8 to 9 hours to produce a red *ginseng* extract.

The extraction step was repeated five times, and the red *ginseng* extracts were produced individually according to the respective extraction times.

Amounts of red *ginseng* extracts produced according to the respective extraction times were listed in Table 2.

TABLE 2

| Extraction times | Red ginseng extract weight (kg) | Red ginseng extract cumulative weight (kg) |
| --- | --- | --- |
| First time | 254 | 254 |
| Second time | 51 | 305 |
| Third time | 26 | 331 |
| Fourth time | 22 | 353 |
| Fifth time | 30 | 383 |

Second Comparison Example: Third Production of Red Ginseng Extract

A red *ginseng* extract was produced from the fresh *ginseng* to which no ultra high pressure treatment was applied.

First Step: Steaming and Drying

The fresh *ginseng* washed according to the first producing example was arranged in a steamer in such a manner as to be not pushed or laminated onto each other, and next, the fresh *ginseng* was steamed through heating at a temperature of 96° C. for 1 hour. After the steaming was finished, a pressure of the steamer was released to remove steam and thus to obtain red *ginseng*.

Next, the red *ginseng* was arranged in a drier in such a manner as to be not pushed or laminated onto each other, and after that, the red *ginseng* was dried through heating at a temperature of 60° C. for 72 to 96 hours.

Second Step: Red*Ginseng*Extract Producing

The red *ginseng* made through the first step was put into an extraction container of an extractor, and also, ethanol as an extraction solvent was put thereinto. Next, the red *ginseng* was heated at a temperature of 46 to 53° C. for 8 to 9 hours to produce a red *ginseng* extract.

The extraction step was repeated five times, and extracts were produced individually according to the respective extraction times.

Amounts of red *ginseng* extracts produced according to the respective extraction times were listed in Table 3.

TABLE 3

| Extraction times | Red ginseng extract weight (kg) | Red ginseng extract cumulative weight (kg) |
| --- | --- | --- |
| First time | 244 | 244 |
| Second time | 50 | 294 |
| Third time | 30 | 324 |
| Fourth time | 22 | 346 |
| Fifth time | 20 | 366 |

First Experimental Example: Analysis of Ingredients of Red*Ginseng*Extract

So as to check the extraction effects of the red *ginseng* extract when the method for processing the *ginseng* according to the present invention is applied, the components of the ginsenosides of the red *ginseng* extracts produced in the first embodiment, the first comparison example, and the second comparison example were compared and analyzed.

The components of the ginsenosides of the red *ginseng* extracts produced in the first embodiment, the first comparison example, and the second comparison example were analyzed according to extraction times by means of an HPLC (High Performance Liquid Chromatography), and the analyzed results were indicated in Tables 4 to 6 (The values of the contents of the ginsenosides in Tables 4 to 6 indicate the mass (g) of the ginsenosides contained in 1 kg of red *ginseng* extract).

TABLE 4

| First embodiment | | \multicolumn{5}{c}{Extraction times} | | | | |
|---|---|---|---|---|---|---|
| Ingredient Name | | First time | Second time | Third time | Fourth time | Fifth time |
| Ginsenoside Content Ratio (g/kg) | Rg1 | 3.44 | 1.88 | 0.1 | 0.01 | 0 |
| | Rb2 | 3.00 | 1.52 | 0.01 | 0 | 0 |
| | Rc | 2.33 | 1.23 | 0.01 | 0.01 | 0 |
| | Rd | 1.23 | 0.66 | 0.05 | 0.01 | 0 |
| | Rg3 | 0.12 | 0.06 | 0.01 | 0.01 | 0 |
| | Re | 1.98 | 0.55 | 0.11 | 0.01 | 0 |
| | Rf | 0.06 | 0.04 | 0.01 | 0.01 | 0 |
| | Rg1 | 1.21 | 0.50 | 0.03 | 0.01 | 0 |
| | Rg2 | 0.55 | 0.11 | 0.01 | 0 | 0 |
| | Rh1 | 0.33 | 0.15 | 0.35 | 0.10 | 0 |
| | Total | 14.25 | 6.70 | 30 | 0.17 | 0 |
| Red ginseng extract (kg) | | 244 | 50 | 30 | 22 | 20 |
| Ginsenoside Content (kg) | | 3705.00 | 341.45 | 11.20 | 5.44 | 0 |

TABLE 5

| First Comparison example | Extraction times | | | | |
|---|---|---|---|---|---|
| Ingredient Name | First time | Second time | Third time | Fourth time | Fifth time |
| Rg1 | 2.88 | 1.95 | 0.12 | 0.01 | 0 |
| Rb2 | 2.05 | 1.02 | 0.02 | 0 | 0 |
| Rc | 2.01 | 0.92 | 0.04 | 0.01 | 0 |

TABLE 5-continued

| First Comparison example | Extraction times | | | | |
|---|---|---|---|---|---|
| Ingredient Name | First time | Second time | Third time | Fourth time | Fifth time |
| Rd | 0.65 | 0.45 | 0.05 | 0 | 0 |
| Rg3 | 0.05 | 0.03 | 0.01 | 0 | 0 |
| Re | 1.36 | 0.55 | 0 | 0 | 0 |
| Rf | 0.06 | 0.03 | 0.01 | 0 | 0 |
| Rg1 | 0.55 | 0.35 | 0.05 | 0.01 | 0 |
| Rg2 | 0.30 | 0.10 | 0.03 | 0 | 0 |
| Rh1 | 0.30 | 0.18 | 0.02 | 0.10 | 0 |
| Total | 10.21 | 5.58 | 0.35 | 0.03 | 0 |
| Red ginseng extract (kg) | 254 | 51 | 26 | 22 | 30 |
| Ginsenoside Content (kg) | 2593.34 | 284.48 | 9.10 | 2.86 | 0 |

TABLE 6

| Second Comparison example | Extraction times | | | | |
|---|---|---|---|---|---|
| Ingredient Name | First time | Second time | Third time | Fourth time | Fifth time |
| Rg1 | 2.01 | 1.25 | 0.88 | 0.02 | 0.02 |
| Rb2 | 1.65 | 0.92 | 0.29 | 0.03 | 0.01 |
| Rc | 1.42 | 14.01 | 0.43 | 0.08 | 0.01 |
| Rd | 0.47 | 0.22 | 0.15 | 0.02 | 0 |
| Rg3 | 0.05 | 0.02 | 0.01 | 0 | 0 |
| Re | 1.22 | 0.45 | 0.20 | 0.05 | 0 |
| Rf | 0.05 | 0.02 | 0.01 | 0 | 0 |
| Rg1 | 0.55 | 0.37 | 0.13 | 0.03 | 0 |
| Rg2 | 0.25 | 0.10 | 0.03 | 0.01 | 0 |
| Rh1 | 0.26 | 0.05 | 0.01 | 0 | 0 |
| Total | 7.93 | 4.41 | 2.14 | 0.34 | 0.04 |
| Red ginseng extract (kg) | 244 | 50 | 30 | 22 | 20 |
| Ginsenoside Content (kg) | 1934.43 | 220.70 | 64.11 | 7.48 | 0.88 |

TABLE 7

| | | Extraction times | | | | |
|---|---|---|---|---|---|---|
| Ingredient Name | | First time | Second time | Third time | Fourth time | Fifth time |
| First embodiment | Ginsenoside Content Ratio (g/kg) | 14.25 | 20.95 | 21.30 | 21.47 | 21.47 |
| | Red ginseng extract (kg) | 260.00 | 311.00 | 343.00 | 375.00 | 397.00 |
| | Ginsenoside Content (kg) | 3705.00 | 4046.45 | 4057.65 | 4063.09 | 4063.09 |
| First Comparison example | Ginsenoside Content Ratio (g/kg) | 10.21 | 15.79 | 16.14 | 16.27 | 16.27 |
| | Red ginseng extract (kg) | 254.00 | 305.00 | 331.00 | 353.00 | 383.00 |
| | Ginsenoside Content (kg) | 2593.34 | 2877.82 | 2886.92 | 2889.78 | 2889.78 |
| Second Comparison example | Ginsenoside Content Ratio (g/kg) | 7.93 | 12.34 | 14.48 | 14.82 | 14.86 |
| | Red ginseng extract (kg) | 244.00 | 294.00 | 324.00 | 346.00 | 366.00 |

TABLE 7-continued

| Ingredient Name | | Extraction times | | | | |
|---|---|---|---|---|---|---|
| | | First time | Second time | Third time | Fourth time | Fifth time |
| | Ginsenoside Content (kg) | 1934.43 | 2155.13 | 2219.24 | 2226.72 | 2227.60 |

FIG. 1 is a graph showing ratios of contents of ginsenosides extracted from the red *ginseng* extracts according to extraction times in the first embodiment, the first comparison example, and the second comparison example, as listed in Tables 4 to 6.

As shown in FIG. 1, it can be appreciated that the ratios of contents of ginsenosides in the first embodiment of the present invention are remarkably higher than those in the first comparison example and the second comparison example.

FIG. 2 is a graph showing ratios of contents of ginsenosides extracted from the red *ginseng* extracts that are accumulated according to extraction times in the first embodiment, the first comparison example, and the second comparison example, as listed in Table 7.

As shown in FIG. 2 and Table 7, it can be appreciated that the red *ginseng* extract according to the first embodiment of the present invention has a ginsenoside content ratio of 20.95 g/kg only through two extraction times. On the other hand, the red *ginseng* extract according to the first comparison example has a ginsenoside content ratio of 15.79 g/kg through two extraction times and a ginsenoside content ratio of 16.27 g/kg through five extraction times, and the red *ginseng* extract according to the second comparison example has a ginsenoside content ratio of 12.34 g/kg through two extraction times and a ginsenoside content ratio of 14.86 g/kg through five extraction times. It can be therefore appreciated that the ginsenoside content ratio of the red *ginseng* extract through the two extraction times in the first embodiment of the present invention is higher than the ginsenoside content ratios of the red *ginseng* extracts through the two extraction times as well as the five extraction times in the first comparison example and the second comparison example. In detail, if the method for applying the ultra high pressure to the immersed and packed *ginseng* according to the present invention is adopted, the red *ginseng* extract produced only through the two extraction times has the ginsenoside content larger than that produced through the five extraction times, while having no ultra high pressure treatment and immersed packing.

If the red *ginseng* extract is produced using the method for processing the *ginseng* according to the present invention, accordingly, it has large contents of ginsenosides just through relatively low extraction times, thereby making the process for producing the red *ginseng* extract simplified and reducing the manufacturing cost through the simplification of the producing process. Even if the red *ginseng* extracts are produced through the same extraction times as each other, moreover, the red *ginseng* extract produced using the method for processing the *ginseng* according to the present invention has larger contents of ginsenosides than that produced from the immersed and packed *ginseng* to which no ultra high pressure treatment is applied, so that the method for processing the *ginseng* according to the present invention can be usefully adopted in producing the red *ginseng* extract.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above teachings. It is therefore intended that the scope of the invention be limited not by this detailed description, but rather by the claims appended hereto.

It is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure.

MODE FOR INVENTION

The detailed explanation of the present invention has been given in the best mode of the present invention as mentioned above.

INDUSTRIAL APPLICABILITY

The present invention relates to the method for processing the *ginseng* at the ultra high pressure, and accordingly, the *ginseng* can be processed in large amounts upon the ultra high pressure treatment, so that the effective ingredients of the *ginseng* or red *ginseng* made through the ultra high pressure treatment can be increased, thereby achieving a high level of industrial applicability.

The invention claimed is:

1. A method for processing *ginseng*, comprising the steps of:
    preparing washed *ginseng*;
    liquid-packaging the *ginseng* into a pouch; and
    treating the liquid-packaged *ginseng* with ultra-high pressure at a pressure of 550 to 600 MPa for 30 seconds to 2 minutes.

2. The method according to claim 1, wherein the liquid-packaging is carried out by putting a solvent and the *ginseng* in the pouch, removing air from the pouch, and sealing the pouch.

3. The method according to claim 2, wherein the solvent is water or ethanol.

4. The method according to claim 1, wherein the pouch is made of one selected from the group consisting of LDPE, LLDPE, HDPE, PP, PS, PVC, SBS, and PE.

5. The method according to claim 1, wherein the pouch has a thickness of 1 to 2 mm.

6. The method according to claim 1, further comprising, after the processing, the steps of:
    steaming the *ginseng* at a temperature of 96 to 98° C. for 1 to 1.2 hours; and drying the steamed *ginseng* at a temperature of 50 to 60° C. for 72 to 96 hours.

7. The method according to claim 6, further comprising, after the drying step, the step of: putting the dried *ginseng* in an extraction solvent, heating the *ginseng* in the extraction solvent at a temperature of 46 to 53° C. for 8 to 9 hours, and producing a *ginseng* extract.

8. The method according to claim 7, wherein the extraction solvent is mixed with the solvent collected after treating the liquid-packaged *ginseng* with the ultra-high pressure.

9. A *ginseng* extract produced by a method for processing *ginseng*, the method comprising the steps of:
preparing washed *ginseng*;
liquid-packaging the *ginseng* into a pouch;
treating the liquid-packaged *ginseng* with ultra-high pressure at a pressure of 550 to 600 MPa for 30 seconds to 2 minutes;
steaming the treated *ginseng* with ultra-high pressure at a temperature of 96 to 98° C. for 1 to 1.2 hours;
drying the steamed *ginseng* at a temperature of 50 to 60° C. for 72 to 96 hours; and
putting the dried *ginseng* in an extraction solvent, heating the *ginseng* in the extraction solvent at a temperature of 46 to 53° C. for 8 to 9 hours, and producing the *ginseng* extract.

10. The *ginseng* extract according to claim 9, containing ginsenoside contents more than 2 wt % through two extraction times.

* * * * *